US010054549B2

(12) United States Patent
Choulet

(10) Patent No.: US 10,054,549 B2
(45) Date of Patent: Aug. 21, 2018

(54) METHOD AND APPARATUS FOR AUTOMATIC MEASUREMENT OF VARIOUS QUALITIES OF PRINTED SHEETS

(71) Applicant: ELECTRONICS FOR IMAGING, INC., Fremont, CA (US)

(72) Inventor: Luc Choulet, Charnay les Macon (FR)

(73) Assignee: ELECTRONICS FOR IMAGING, INC., Fremont, CA (US)

(*) Notice: Subject to any disclaimer, the term of this patent is extended or adjusted under 35 U.S.C. 154(b) by 0 days.

(21) Appl. No.: 14/151,703

(22) Filed: Jan. 9, 2014

(65) Prior Publication Data

US 2015/0192516 A1 Jul. 9, 2015

(51) Int. Cl.
*G01J 3/46* (2006.01)
*G01N 21/86* (2006.01)
*G01N 21/57* (2006.01)
*G01N 21/55* (2014.01)
*G01N 21/59* (2006.01)
*G01N 21/25* (2006.01)
*G01N 21/47* (2006.01)

(52) U.S. Cl.
CPC .............. *G01N 21/86* (2013.01); *G01J 3/46* (2013.01); *G01N 21/255* (2013.01); *G01N 21/55* (2013.01); *G01N 21/57* (2013.01); *G01N 21/59* (2013.01); *G01N 2021/4719* (2013.01); *G01N 2021/4742* (2013.01); *G01N 2021/575* (2013.01); *G01N 2021/8663* (2013.01)

(58) Field of Classification Search
CPC ............ G01J 3/46; G01J 3/501; G01J 3/0254; G01N 21/57; G01N 21/55; G01N 21/251

USPC ............... 356/445–448, 319, 326, 402, 407; 358/1.9, 3.06, 504
See application file for complete search history.

(56) References Cited

U.S. PATENT DOCUMENTS

| 4,003,660 A * | 1/1977 | Christie, Jr. ........ B41F 33/0036 250/226 |
| 4,671,661 A * | 6/1987 | Ott ...................... B41F 33/0036 235/454 |
| 5,015,098 A * | 5/1991 | Berg ................... G01N 21/274 356/402 |
| 5,142,337 A | 8/1992 | Karidis et al. |
| 5,182,721 A * | 1/1993 | Kipphan ............. B41F 33/0045 101/484 |
| 5,347,288 A * | 9/1994 | Page .................... H01Q 3/2676 342/374 |

(Continued)

FOREIGN PATENT DOCUMENTS

| EP | 2078613 A2 | 7/2009 |
| EP | 2301757 A1 | 3/2011 |
| FR | 2983951 A1 | 6/2013 |

OTHER PUBLICATIONS

"ColorThink Pro", CHROMiX ColorThink, retrieved online on Mar. 12, 2013 from url: http://www2.chromix.com/colorthink/pro/pro_colorcast; 2 pages, undated, 2 pages.

(Continued)

*Primary Examiner* — Hoa Pham
(74) *Attorney, Agent, or Firm* — Perkins Coie LLP

(57) ABSTRACT

Embodiments of the invention relate to the automatic measuring of such qualities of a printed sheet as reflectance excluding specular reflectance, reflectance including specular reflectance, e.g. gloss, transmittance, half-tone coverage, and the like.

6 Claims, 18 Drawing Sheets

(56) References Cited

U.S. PATENT DOCUMENTS

| | | | |
|---|---|---|---|
| 5,370,976 A | 12/1994 | Williamson et al. | |
| 5,387,977 A * | 2/1995 | Berg | G01J 3/02 250/227.3 |
| 5,822,503 A | 10/1998 | Gass et al. | |
| 6,707,479 B1 | 3/2004 | Pan et al. | |
| 6,707,553 B1 | 3/2004 | Imura | |
| 6,944,334 B2 | 9/2005 | Piatt et al. | |
| 7,920,297 B2 | 4/2011 | Doggett, III et al. | |
| 8,472,831 B2 | 6/2013 | Bettiol et al. | |
| 8,711,432 B2 * | 4/2014 | Ito | H04N 1/54 358/1.9 |
| 8,743,137 B2 | 6/2014 | Peters et al. | |
| 2001/0024274 A1 * | 9/2001 | Shimizu | G01J 3/28 356/326 |
| 2002/0191188 A1 * | 12/2002 | Hubble, III | G01J 3/02 356/402 |
| 2003/0058447 A1 * | 3/2003 | Yamada | G01J 3/02 356/402 |
| 2003/0098986 A1 | 5/2003 | Pop | |
| 2003/0169421 A1 | 9/2003 | Ehbets | |
| 2003/0184002 A1 * | 10/2003 | Akiyama | B65H 3/0669 271/110 |
| 2004/0027416 A1 | 2/2004 | Rosenberger et al. | |
| 2004/0051874 A1 | 3/2004 | Kubitzek et al. | |
| 2004/0233463 A1 | 11/2004 | Hersch et al. | |
| 2005/0052670 A1 | 3/2005 | Nishikawa et al. | |
| 2005/0073571 A1 | 4/2005 | Pan et al. | |
| 2005/0128496 A1 | 6/2005 | Bala | |
| 2005/0248789 A1 * | 11/2005 | Kita | G03G 15/5062 358/1.9 |
| 2005/0286085 A1 | 12/2005 | Lee | |
| 2006/0082844 A1 | 4/2006 | White | |
| 2007/0201062 A1 | 8/2007 | Watanabe | |
| 2009/0284772 A1 | 11/2009 | Sai et al. | |
| 2010/0134811 A1 | 6/2010 | Fukasawa et al. | |
| 2010/0177327 A1 | 7/2010 | Maheshwari | |
| 2011/0149316 A1 * | 6/2011 | Omagari | H04N 1/00002 358/1.9 |
| 2011/0234660 A1 | 9/2011 | Yoshida | |
| 2012/0081461 A1 | 4/2012 | Kakutani | |
| 2012/0105882 A1 | 5/2012 | Horita et al. | |
| 2012/0263512 A1 | 10/2012 | Sakai et al. | |
| 2012/0320393 A1 | 12/2012 | Ito et al. | |
| 2013/0188186 A1 * | 7/2013 | Okumura | G01J 3/46 356/402 |

OTHER PUBLICATIONS

Stone, et al., "Color Gamut Mapping and the Printing of Digital Color Images", (1988)Journal of ACM Transactions on Graphics (TOG). vol. 7, Issue 4, 44 Pages.

"Collimators and Focusers—Pigtail Style", OZ Optics; retrieved online from url www.ozoptics.com/ALLNEW_PDF/DTS0060.pdf, Feb. 19, 2005, 4 pages.

* cited by examiner

METHOD AND APPARATUS FOR AUTOMATIC MEASUREMENT OF VARIOUS QUALITIES OF PRINTED SHEETS

BACKGROUND OF THE INVENTION

Technical Field

The invention relates to printing. More particularly, the invention relates to the measuring of qualities of a printed sheet, for example, reflectance excluding specular reflectance, reflectance including specular reflectance, e.g. gloss, transmittance, and half-tone coverage.

Description of the Background Art

Many factors affect the qualities of an image that is printed on a sheet. Such phenomena as reflection and transmittance of light occur because the frequencies of the light waves do not match the natural frequencies of vibration of the objects. When light waves of these frequencies strike an object, such as a sheet of paper, the electrons in the atoms of the object begin vibrating. But instead of vibrating in resonance at a large amplitude, the electrons vibrate for brief periods of time with small amplitudes of vibration; then the energy is reemitted as a light wave. If the object is transparent, then the vibrations of the electrons are passed on to neighboring atoms through the bulk of the material and reemitted on the opposite side of the object. Such frequencies of light waves are said to be transmitted. If the object is opaque, then the vibrations of the electrons are not passed from atom to atom through the bulk of the material.

Rather the electrons of atoms on the material's surface vibrate for short periods of time and then reemit the energy as a reflected light wave. Such frequencies of light are said to be reflected.

The color of the objects that we see is largely due to the way those objects interact with light and ultimately reflect or transmit it to our eyes. The color of an object is not actually within the object itself. Rather, the color is in the light that shines upon it and is ultimately reflected or transmitted to our eyes. The visible light spectrum consists of a range of frequencies, each of which corresponds to a specific color. When visible light strikes an object and a specific frequency becomes absorbed, that frequency of light never makes it to our eyes. Any visible light that strikes the object and becomes reflected or transmitted to our eyes contributes to the color appearance of that object. Thus, the color is not in the object itself, but in the light that strikes the object and ultimately reaches our eye. The only role that the object plays is that it might contain atoms capable of selectively absorbing one or more frequencies of the visible light that shine upon it. If an object absorbs all of the frequencies of visible light except for the frequency associated with green light, then the object appears green in the presence of visible light. If an object absorbs all of the frequencies of visible light except for the frequency associated with blue light, then the object appear blues in the presence of visible light.

Reflectivity is a directional property. Most surfaces can be divided into those that give specular reflection and those that give diffuse reflection. For specular surfaces, such as glass or polished metal, reflectivity is nearly zero at all angles except at the appropriate reflected angle. That is, reflected radiation follows a different path from incident radiation for all cases other than radiation normal to the surface. For diffuse surfaces, such as matte white paint, reflectivity is uniform; radiation is reflected in all angles equally or near-equally. Such surfaces are said to be Lambertian. Most real objects have some mixture of diffuse and specular reflective properties.

Gloss is an optical property describing the ability of a surface to reflect light into the specular direction. The factors that affect gloss are the refractive index of the material, the angle of incident light and the surface topography. Gloss is one of the factors that describe the visual appearance of an object. Factors that affect gloss include, for example, the refractive index of the material, the angle of incident light relative to the surface of the material, and the material's surface topography. Very rough surfaces, such as chalk reflect no specular light and appear dull. Gloss is also expressed as luster in mineralogy, or sheen in certain fields of application.

The appearance of gloss depends on a number of parameters which include the illumination angle, refractive index, surface condition, and observer characteristics. Primarily light is reflected from a surface in one of two ways. In specular reflection, the angle of the light reflected from the surface is equal and opposite to the angle of the incident light. A diffuse reflection scatters the incident light over a range of directions. Variations in surface texture influence specular reflectance levels. Objects with a fine surface texture, i.e. highly polished and smooth, allow a high percentage of light to be reflected from their surfaces making them appear shiny to the eye. This is due to a greater amount of incident light striking the surface being reflected directly back to the observer; the majority of which being reflected in the specular direction.

Conversely, objects with rough surfaces cause the light to be deflected at different angles according to the surface profile resulting in a scattering of light away from the angle of reflection. This causes the object to appear dull or matte. The image forming qualities are much lower making any reflection appear blurred. The higher the degree of surface roughness, the greater the scattering of light resulting in a lower gloss level.

Due to the refractive index, the type of substrate material also has an important effect on the amount of specular reflection from its surface. Nonmetallic materials such as dielectrics and insulators, i.e. plastics and coatings, produce a higher level of reflected light when illuminated at a greater illumination angle due to light being absorbed into the material or being diffusely scattered depending on the color of the material. Metals, e.g. conductors, do not suffer from this effect producing higher amounts of reflection at any angle than nonmetals Further, many different phenomena influence the reflection spectrum of, for example, a color halftone patch printed on a diffusely reflecting substrate, e.g. paper. These phenomena comprise the surface reflection at the interface between the air and the paper, light scattering and reflection within the substrate, i.e. paper bulk, and the internal reflections at the interface between the paper and the air. The lateral scattering of light within the paper substrate and the internal reflections at the interface between the paper and the air are responsible for what is generally called the optical dot gain. In addition, due to the printing process, the deposited ink surface coverage is generally larger than the nominal coverage, yielding a physical or mechanical dot gain. Effective ink surface coverage depend on the inks, on the paper, and also on the specific superposition of the different inks.

As can be seen from the foregoing, the physics of light in connection with the printing of an image on a sheet is complex. It would be advantageous to be able to measure any one or more of the foregoing qualities quickly and accurately in situ and use the results of such measurements to enhance the process of printing in both real time and to parameterize the printing process.

SUMMARY OF THE INVENTION

Embodiments of the invention relate to the automatic measuring of such qualities of a printed sheet as reflectance excluding specular reflectance, reflectance including specular reflectance, e.g. gloss and metallic reflectance, transmittance, half-tone coverage, and the like.

In an embodiment, a computer implemented method is provided for automatic measurement of reflectance, in which one or more spectral sensors are used to measure spectral reflectance at at least multiple angles, e.g. typically two to five angles, relative to a sheet for each of a plurality of colored patches on said sheet (fingerprint). For purposes of the discussion herein, a fingerprint is embodied in a standardized or customized print target that can have up to hundreds of color patches, made by a combination of mixing primary colors. All of these combinations are generally limited, e.g. by sub-sampling, in comparison to the total quantity of combinations drivable by the device, e.g. ≈1000 combinations for 4294 billions ($256^4$) if printing with four colors.

Printing this sub-sampled device combination results in, after printing and measurement, a sub-sampled color description of the device in a certain configuration, e.g. media, screens, ink density, hardware setting, etc.

Then, a color look-up table (CLUT) is computed to define the colorimetric value generated by a device color combination. The reserve CLUT, e.g. colorimetric space to printer device, is also computed. These CLUTs could be saved as a ICC profile. Many methods for creating ICC profiles could be used. The ICC profile file is used to predict the color of a certain device combination and to define a device combination for reproducing a certain color. In embodiments of the invention, the colored patches on the sheet are produced in accordance with the fingerprint of the printer, as determined by the foregoing technique.

In embodiments of the invention, the spectral measurements are processed by a single angle per measurement, where a next angle is measured after a full measurement of the sheet for a previous angle. In this embodiment, measurement of each patch is performed by moving any of the sheet, the sensor, or both, preferably in other than X, Y coordinates.

In another embodiment, a computer implemented method is provided for automatic measurement of reflectance excluding specular reflectance and reflectance including specular reflectance, in which a spectral sensor is used to measure light reflectance at one angle chosen for excluding specular reflectance, to quantify spectral reflectance in the visible wavelength, e.g. 400 to 700 nm, for each of a plurality of colored patches on a sheet (fingerprint). Three or more sensors are arranged in different angles relative to the sheet for simultaneously measuring gloss (1D space) for each of the plurality of colored patches on the sheet. In this embodiment, measurement of each patch is performed by moving any of the sheet, the sensor, or both, preferably in other than X, Y coordinates.

In another embodiment, a computer implemented method is provided for automatic measurement of reflectance and transmittance, in which a single spectral sensor is used for substantially simultaneously measuring both spectral reflectance and spectral transmittance for each of a plurality of colored patches on a sheet (fingerprint). In this embodiment, measurement of each patch is performed by moving any of the sheet, the sensor, or both, preferably in other than X, Y coordinates.

In another embodiment, a computer implemented method is provided for automatic measurement of reflectance and halftone coverage of a sheet surface, in which a spectral sensor is used to measure spectral reflectance for each of a plurality of colored patches on a sheet (fingerprint), and in which with a color camera is used for simultaneously measuring halftone coverage of a surface of the sheet. A processor uses these measurements of halftone coverage of a surface of the sheet and applies a numerical filter (color) to perform image analysis and thus determine a threshold estimate of surface coverage by an ink dot. In this embodiment, measurement of each patch is performed by moving any of the sheet, the sensor, or both, preferably in other than X, Y coordinates.

In another embodiment, a computer implemented method is provided for automatic substrate detection in which a spectral sensor is used for detecting automatically what type of substrate is in a printer by measuring each of reflectance, transparency, and specular reflectance and/or gloss (three angles) using a light source comprising any of visible light similar to daylight (one source) or at least two colored light sources. Responsive to such substrate detection, the method automatically loads a new technical setup into the printer and/or provides a warning to a user. A combination of all information obtained by these measurements results in a unique ID for each substrate. These measurements are then processed to estimate any of substrate color, substrate opacity, substrate gloss/mat scale, and substrate roughness or texture.

DETAILED DESCRIPTION OF THE INVENTION

Figure 1A:
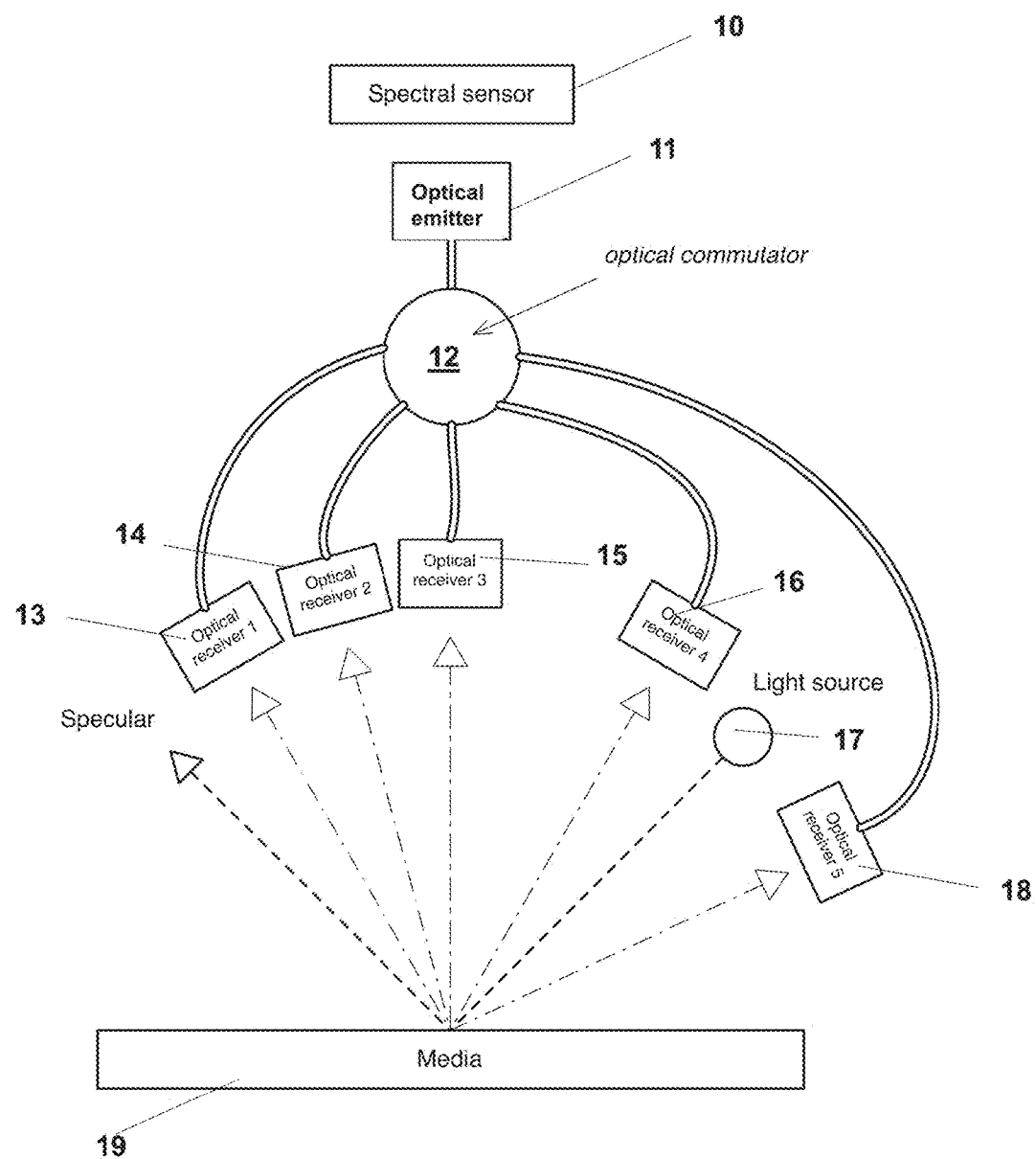
FIG. 1A is a block schematic diagram showing automatic measurement of spectrum reflectance for five angles for all the colored patches present on one sheet according to a first embodiment of the invention.

Embodiments of the invention relate to measuring such qualities of colored surfaces on a flat media, e.g. a printed sheet, as intensity, colorimetric or spectral reflectance, specular reflectance, e.g. gloss, intensity, colorimetric or spectral transmittance, half-tone coverage, and the like. These embodiments include methods and apparatus for the measurement of:

Light reflectance excluding specular reflectance, for spectral and/or colorimetric and/or intensity quantification;
Light reflectance including specular reflectance, for gloss index and/or metallic index and/or intensity quantification;
Light transmittance, for spectral and/or colorimetric and/or intensity quantification; and
Half tone coverage of a surface, and substrate detection.
Each of these embodiments is discussed below.

Automatic Multi-Angle Apparatus for the Measurement of Reflectance

Manual measurement of reflectance is known for large apertures (Ø20 mm), for example for automotive coatings, e.g. see the XRITE MA98 and GARDNER BYK MAC products. Automatic measurement of reflectance is also known for one angle, e.g. see the BARBIERI Spectro LFP product. However, such known approaches are of limited, if any, value for making measurements with a printer, e.g. for a Vutek printer, for measuring reflectance, for example, of silver inks (color calibration), or for measuring reflectance of gloss and/or mat varnish, e.g. the influence of the varnish on the underlying color.

An embodiment of the invention provides an automatic multi-angle apparatus for the measurement of reflectance (FIG. 1). A presently preferred embodiment provides automatized measurement of reflectance for spectral and/or colorimetric and/or intensity quantification by five angles for all the colored patches present on one sheet (fingerprint).

For purposes of the discussion herein, a fingerprint is embodied in a standardized or customized print target that can have up to hundreds of color patches, made by a combination of mixing primary colors. All of these combinations are generally limited, e.g. by sub-sampling, in comparison to the total quantity of combinations drivable by the device, e.g. ≈1000 combinations for 4294 Billions (256^4).

Printing this sub-sampled device combination results in, after printing and measurement, a sub-sampled color description of the device in a certain configuration, e.g. media, screens, ink density, hardware setting, etc.

Then, a color look-up table (CLUT) is computed to define the colorimetric value generated by a device color combination. The reserve CLUT is also computer for the colorimetric space to the printer device. These CLUTs could be saved as a ICC profile. Many methods for creating ICC profiles could be used. The ICC profile file is used to predict the color of a certain device combination and to define a device combination for reproducing a certain color. In embodiments of the invention, the colored patches on the sheet are produced in accordance with the fingerprint of the printer, as determined by the foregoing technique.

FIG. 1A is a block schematic diagram showing automatic measurement of spectrum reflectance for five angles for all the colored patches present on one sheet according to a first embodiment of the invention. As shown in FIG. 1A, at least one spectral sensor 10 is used to make spectral reflectance measurements. The system processes these measurements by one angle per measurement. An optical emitter 11, coupled to an optical commutator 12 communicates each measured signal to the spectral sensor from each of five optical receivers 13, 14, 15, 16, 18. The optical receivers measure reflectance of light from a light source 17 from the surface of a measured medium 19.

Figure 1B:
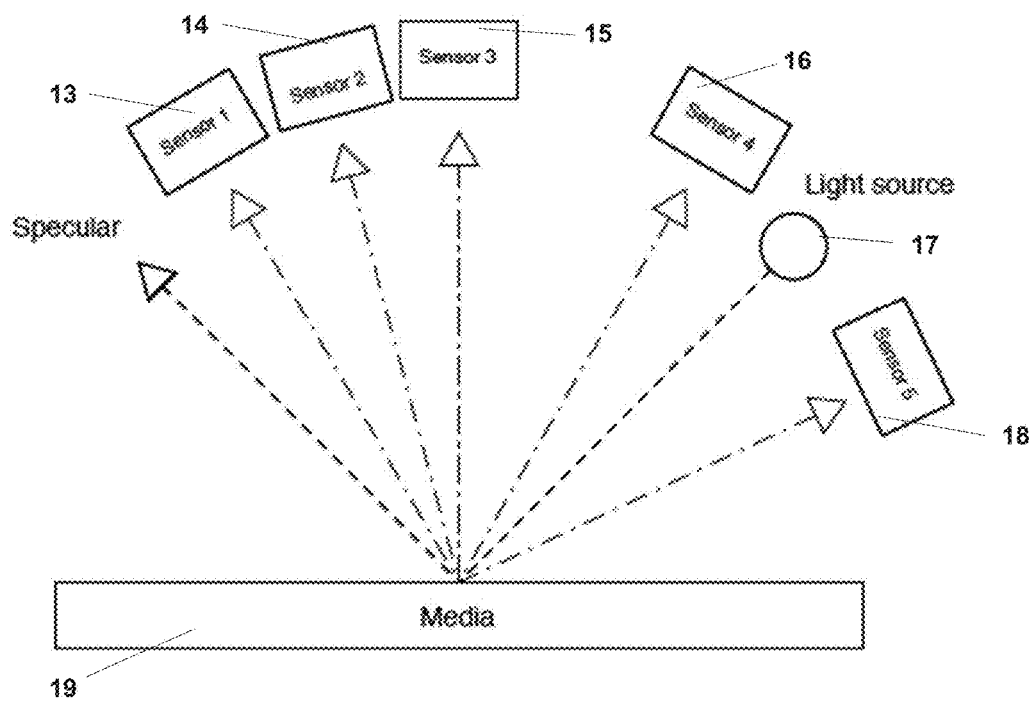
FIG. 1B is a block schematic diagram showing automatic measurement of spectrum reflectance for five angles for all the colored patches present on one sheet according to an alternative embodiment of the invention.

FIG. 1B is a block schematic diagram showing automatic measurement of spectrum reflectance for five angles for all the colored patches present on one sheet according to an alternative embodiment of the invention. As shown in FIG. 1B, in some case, such as decreasing the cost of the device and/or increasing the speed of measurement, it is not necessary to have spectral reflectance for all o the angles. In this embodiment, only sensor 3 (15), i.e. having a normal angle to the surface and 45° to the light source 17, is needed as a spectral sensor. In this embodiment, light transfer could use, if needed, an optical fiber and/or lens and optical components. For the other angles and/or other sensors, it is possible to use colorimetric sensors, e.g. to measure three bands with a standardized RGB filter, for the other angles; and a light intensity sensor, such as a photodiode, having one wide band centered around 550 nm, for the other angles. In such case, it is necessary to compute a ratio by taking the normal angle as reference (sensor 3=45/0°).

For the colorimetric sensor, six data points could be used:
One set of spectral reflectance at the normal angle with the media; and
One colorimetric value computed from spectral reflectance at the normal angle with the media, and one colorimetric value per the other angles.

For light intensity sensor, six data points could be used:
One set of spectral reflectance values at the normal angle with the media; and
One light intensity value computed from spectral reflectance at the normal angle with the media, and one light intensity value per the other angles.

Figure 2:
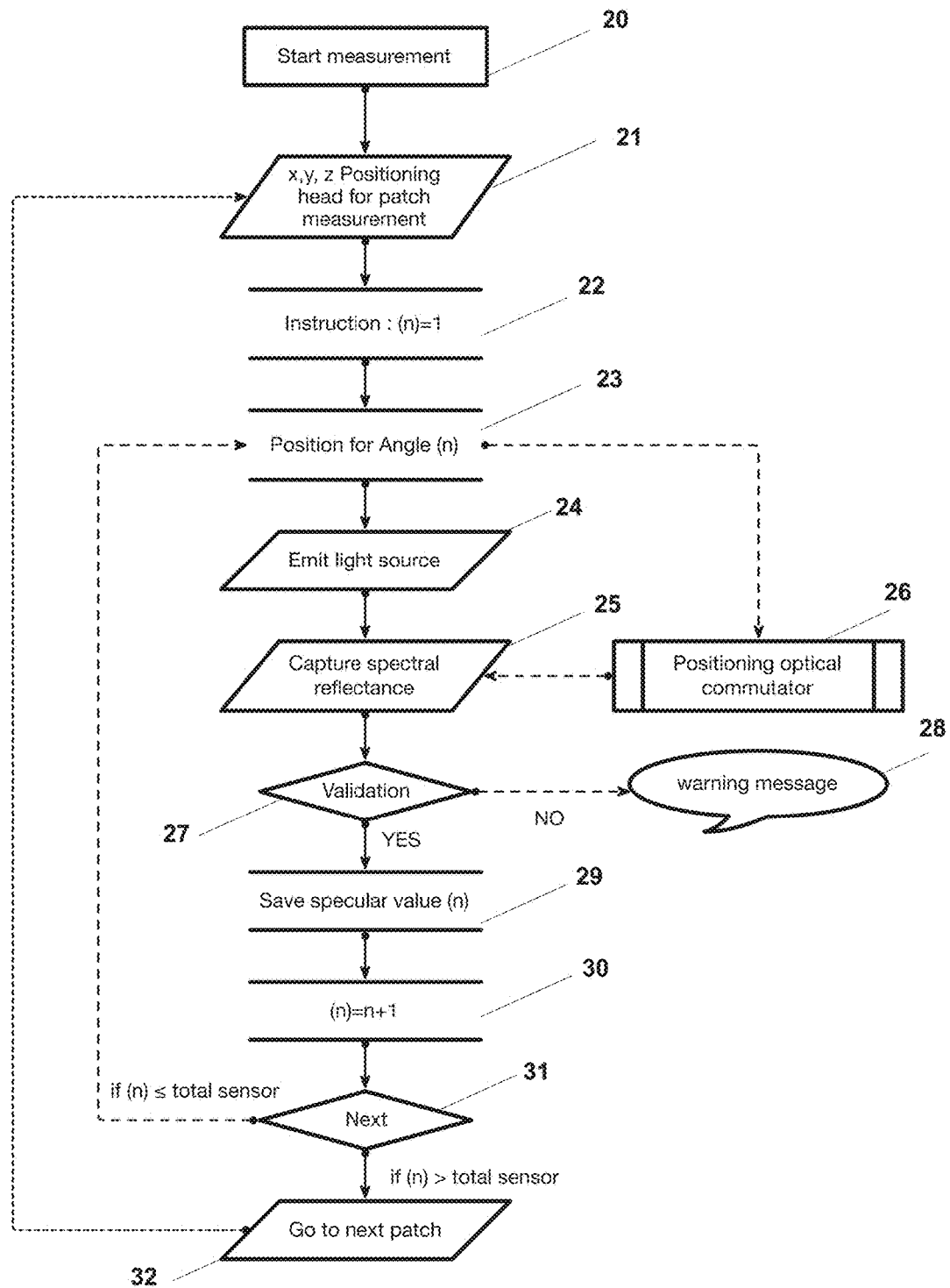
FIG. 2 is a flow diagram that shows a technique for making spectral reflectance measurements according to the invention.

FIG. 2 is a flow diagram that shows a technique for making spectral reflectance measurements according to the invention. In FIG. 2, the measurement sequence begins 20 and x, y, z, positioning of the print head is performed for patch measurement 21. In instruction specifies the measurement, starting with (n)=1 22. The head is positioned for angle (n) 23 and light is emitted from the light source 24. The spectral reflectance is captured 25. The measurement is validated 27 and, if not valid, a warning message is sent 28; else, the specular value is saved 29 and the value (n) is incremented 30 to allow a next measurement to be made 31. For such subsequent measurements at different angles the optical commutator is positioned 26. The process then otherwise proceeds as outlined above for each sensor.

Figure 3:
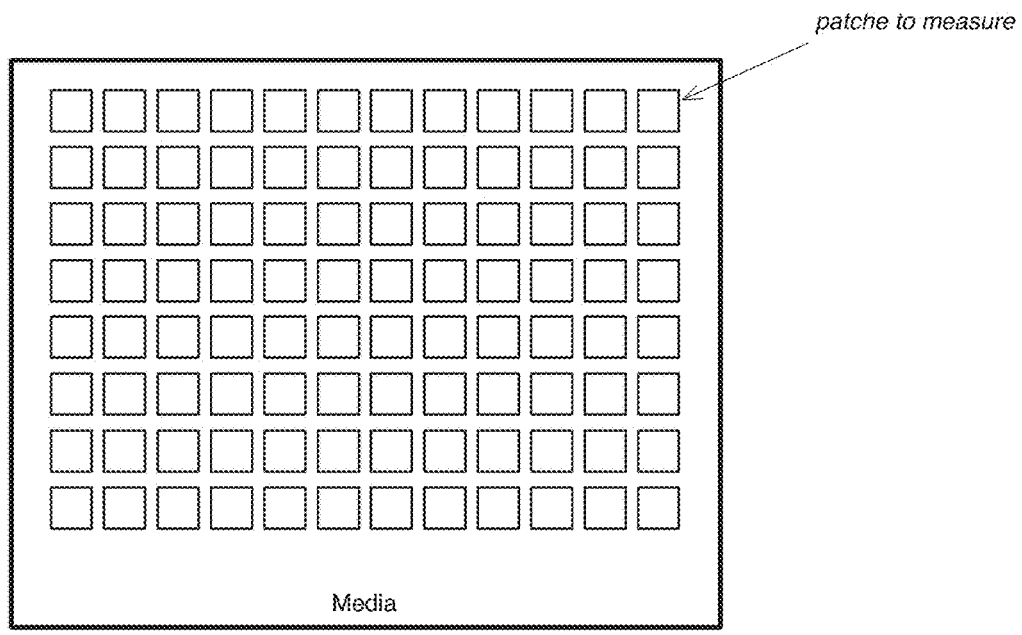
FIG. 3 is a schematic representation of a sheet having a plurality of patches thereon according to the invention.

When a measurement has been made for each sensor, such that the value of (n) equals the total number of sensors, measurements are made at a next patch on the substrate 31. Thus, a new angle is measured after a full measurement of the sheet, i.e. first angle A is measured for all the patches, then angle B is measured, etc. In an embodiment, an optical fiber is used to send light to the sheet and return light from the sheet. Further, in a presently preferred embodiment, the size of the patch measured should be less than 6×6 mm. The measurement of each patch is performed by a movement of the sheet, of the sensor, or both by a set of stepping motors in a mode that is preferably not X, Y. FIG. 3 is a schematic representation of a sheet having a plurality of patches thereon according to the invention.

Figure 4A:
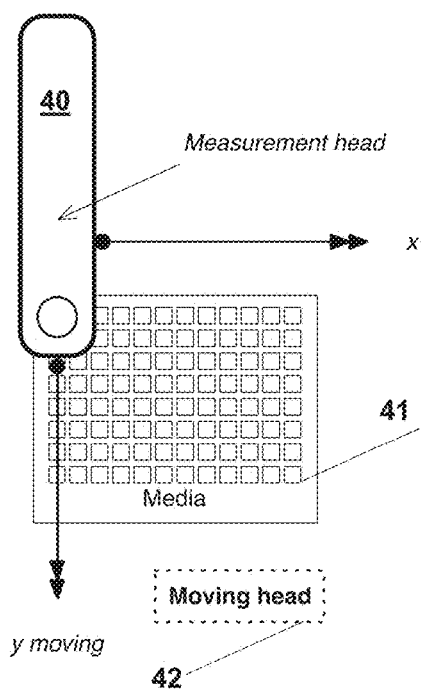
FIGS. 4A and 4B are schematic diagrams showing alternate embodiments of a measurement mechanism for a measurement device having a moving head (FIG. 4A) and a measurement device having a moving sheet (FIG. 4B) according to the invention.
Figure 4B:
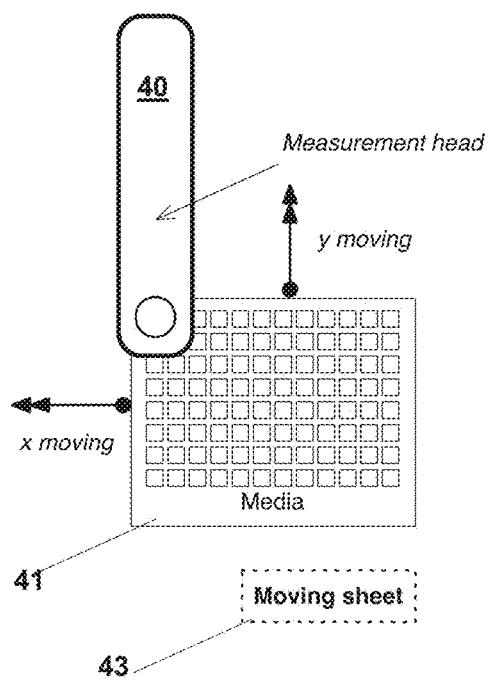

FIGS. 4A and 4B are schematic diagrams showing alternate embodiments of a measurement mechanism for a device measurement having a moving head (FIG. 4A) and a device measurement having a moving sheet (FIG. 4B) according to the invention. In FIG. 4A, a measurement head 40 is placed for movement as part of a moving head assembly 42 in the x and y directions relative to a sheet having a plurality of patches formed thereon 41. In FIG. 4B, a measurement head 40 is placed in a stationary arrangement and a sheet having a plurality of patches formed thereon 41 is positioned in the x and y directions relative to the measurement head by a moving sheet assembly 43

Automatic Multi-Angle Apparatus for the Measurement of Visible Spectral Reflectance and Specular Reflectance Manual measurement of specular gloss is known for large apertures, e.g. Ø 20 mm, from a single angle, for example for automotive coatings, e.g. see the GARDNER spectro-guide product, which measures 45/0 gloss. However, such known approaches are of limited, if any, value for making measurements with a printer, e.g. for a Vutek printer, for measuring reflectance, for example, of silver inks (color calibration), or for measuring reflectance of gloss/mat varnish, e.g. the influence of the varnish on the underlying color.

An embodiment of the invention provides an automatic multi-angle apparatus for the measurement of specular reflectance excluding specular light, and spectral or colorimetric or intensity reflectance including specular light. In a presently preferred embodiment, automatic measurement is made of light reflectance for color (spectral space) and gloss (1D space) for all the colored patches present on one sheet (fingerprint). See FIGS. 3, 4A, and 4B. Embodiments of the invention include, for example, a moving head in the x, y axis with a static sheet; a moving sheet in the x, y axis with a static head; and a combination of movements, including a moving head and a moving sheet in the x, y axis To adjust the distance between the measuring head and the sheet, a z movement is needed, this is accomplished manually, by operation of a motor, or by a combination of both. The movement of the head and/or sheet is effected in accordance with the size of the patch and the distance between each patch. In embodiments of the invention, this information includes, for example, defining movement before the measurement is made as coordinates in a file, e.g. x, y, x size, y size, that are sent to the printer to provide instructions for removal and carriage movement; or using an optical detector for carriage movement, e.g. where patch transition is detected by contrast between the patches and the sheet and/or by a high contrast grid, for example a line in black printed on a white substrate.

In an embodiment, color is measured for one angle, e.g. 45/0° and gloss is measured for three or more angles. One spectral sensor is used to measure color and three or more sensors are arranged in different angles to measure light only (one dimension) for gloss information.

Figure 5:
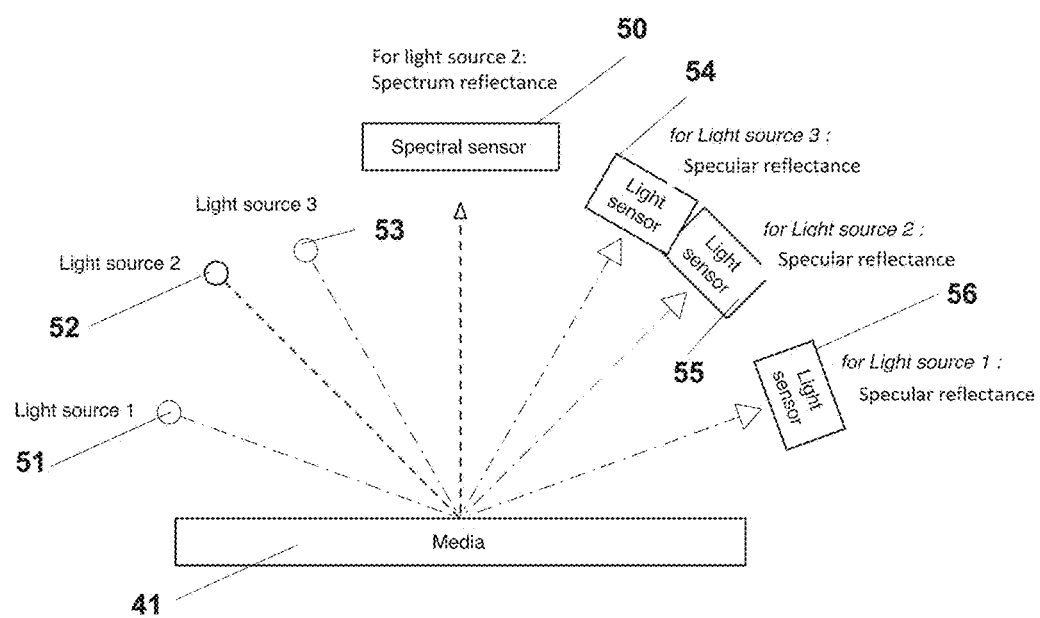
FIG. 5 is a block schematic diagram that shows a mechanism for specular reflectance measurement and spectral reflectance excluding specular reflectance according to the invention.

FIG. 5 is a block schematic diagram that shows a mechanism for spectral measurement according to the invention. In FIG. 5, a plurality of light sources 51, 52, 53, are placed at different angles relative to the surface of the media 41. Respective light sensors 56, 55, 54, collect light from these lights sources as it is reflected from the surface of the media. A spectral sensor 50 is also provided to collect color information with regard to light from, for example light source 2 (52), that is reflected by the media.

In an embodiment, an optical fiber is used to send light to the sheet and return light from the sheet. Further, in a presently preferred embodiment, the size of the patch measured should be less than 6×6 mm. The measurement of each patch is performed by a movement of the sheet, of the sensor, or both by a set of stepping motors in a mode that is preferably not X, Y.

Figure 6:
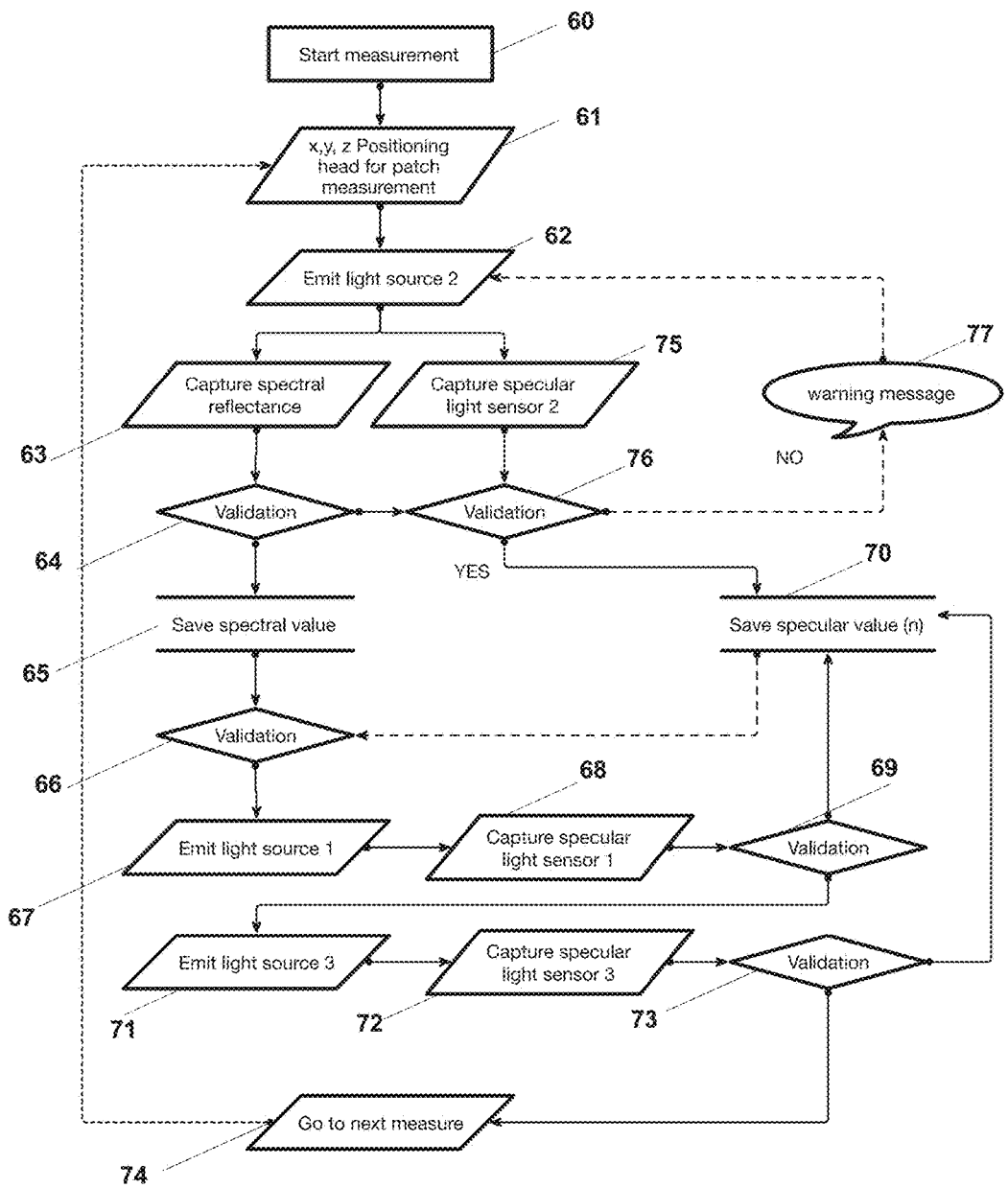
FIG. 6 is a flow diagram that shows the measurement of specular reflectance measurement and spectral reflectance excluding specular reflectance with multiple light sources at multiple angles relative to the media surface according to the invention.

FIG. 6 is a flow diagram that shows the measurement of spectral reflectance for multiple light sources at multiple angles relative to the media surface according to the invention. In FIG. 6, measurement is commenced 60 and x, y, z positioning of the head is effected for patch measurement 61. Light is emitted from the light source that is used for the spectral reflectance measurement 62, in this case light source 2. Spectral reflectance is captured by a corresponding specular sensor 63 and a validation is performed 64. If validation is successful, the spectral value is saved 65. Specular light is also captured from this light source 75 and a validation is performed 76. If successful, the specular value is saved 70, else a warning message is sent 77.

After the spectral reflectance value is saved 65, a further validation is performed to confirm that the value was successfully saved 66. If so, the light is emitted from another light source 67, in this case light source 1. Specular light is captured for this lights source by a corresponding specular sensor 68 and a validation is performed 69. If validation is successful, then the value is saved 70 and light is emitted from another light source 71, in this case light source 3. Specular light is captured for this lights source by a corresponding specular sensor 72 and a validation is performed 73. If validation is successful, then the value is saved 70, the next patch is measured 74, and the process repeats.

Embodiments of the invention provide a low cost solution when compared to devices that are used for multi-angle spectral measurement, and the invention is thus preferably dedicated for measurement of glossy/specular effects.

Apparatus and Process for the Measurement of Reflectance and Transmittance in One Phase An embodiment of the invention provides an apparatus and process for the measurement of reflectance and transmittance. In an embodiment, an automatized measurements of spectral reflectance and spectral transmittance are made simultaneously for one or all of the colored patches present on one sheet (fingerprint). In a presently preferred embodiment, one spectral sensor is used for the two measurements, i.e. for reflectance and transmittance.

Figure 7:
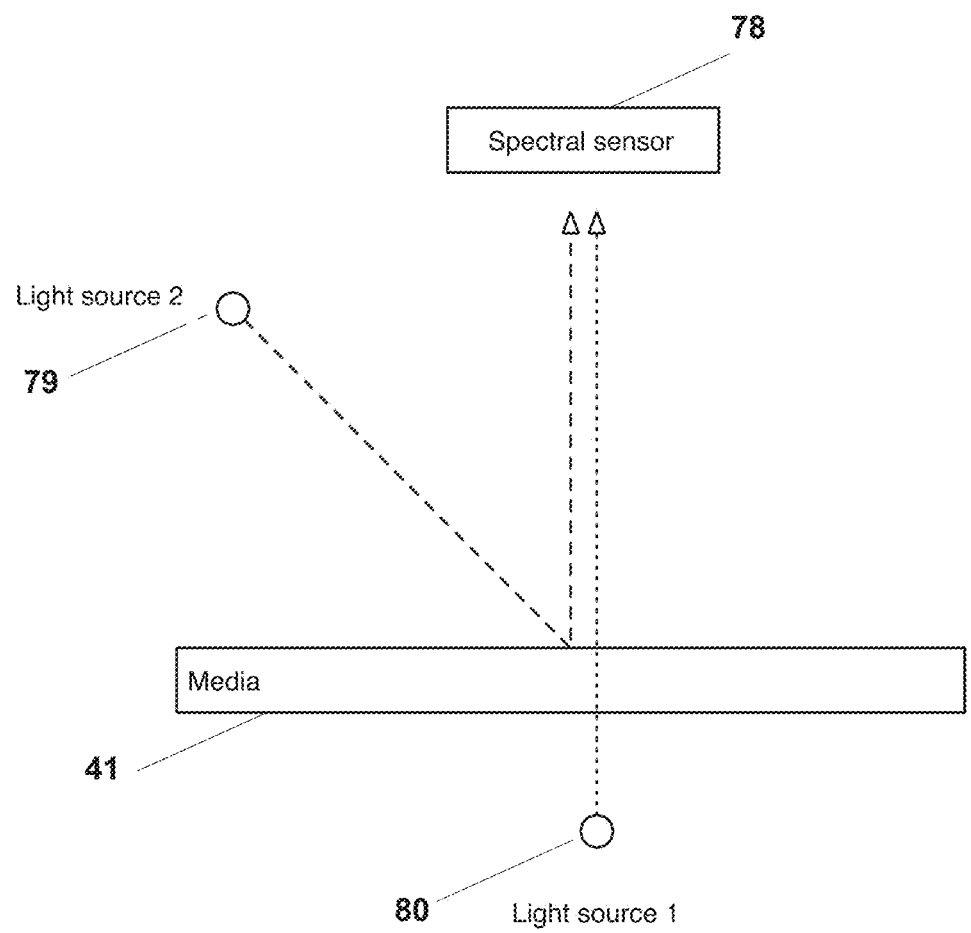
FIG. 7 is a block schematic diagram that shows a mechanism for measuring reflectance and transmittance with one spectral sensor according to the invention.

FIG. 7 is a block schematic diagram that shows a mechanism for measuring reflectance and transmittance with one spectral sensor according to the invention. In FIG. 7, a first light source 79 illuminates the surface of the media 41 and light reflected from the surface of the media is captured by the spectral sensor 70 for purposes of measuring reflectance; a second light source 80 positioned at a back of the media illuminates the media and light transmitted through the media is captured by the spectral sensor for purposes of measuring transmittance.

Figure 8:
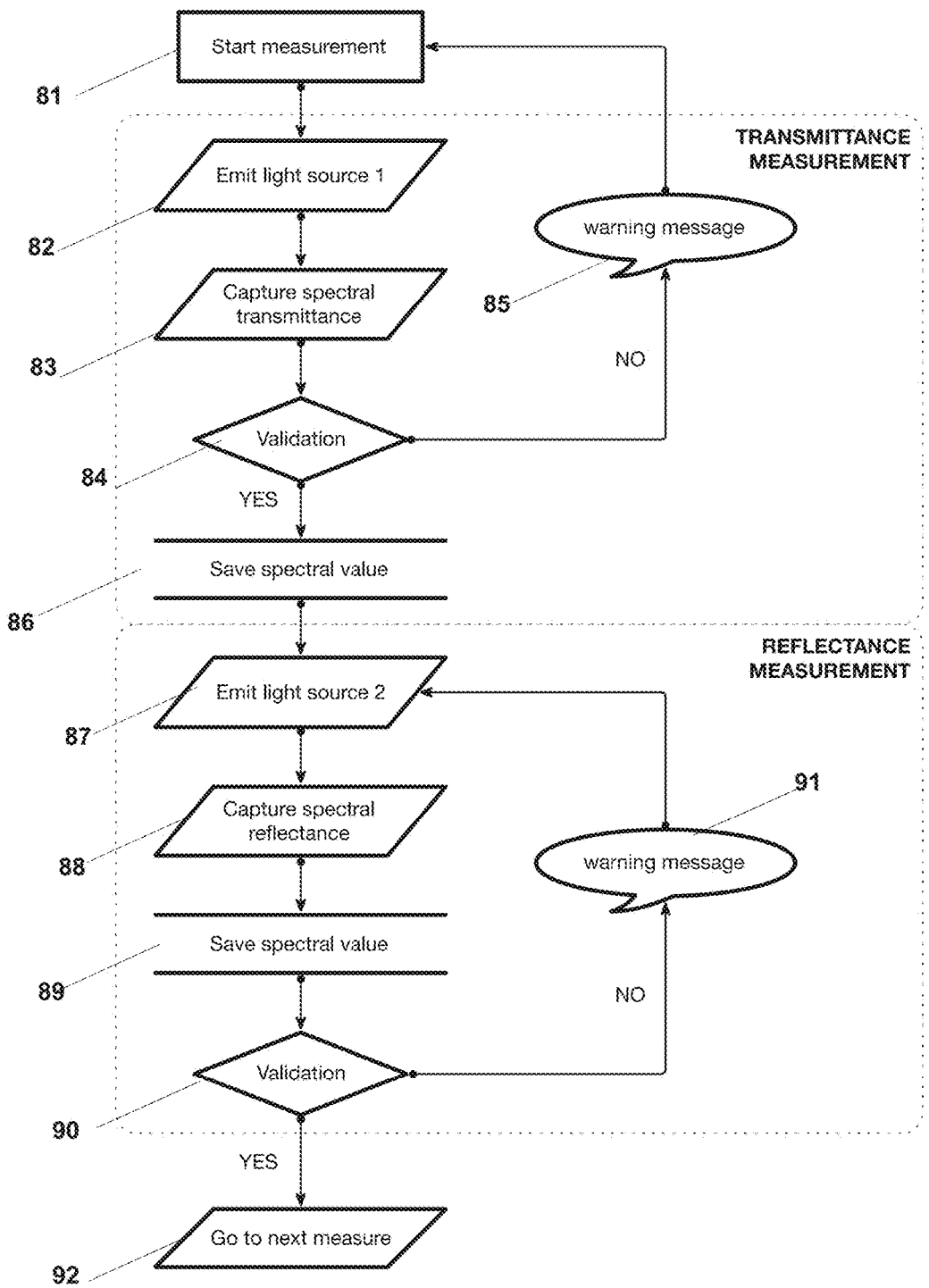
FIG. 8 is a flow diagram that shows the measurement of reflectance and transmittance with one spectral sensor according to the invention.

FIG. 8 is a flow diagram that shows the measurement of reflectance and transmittance with one spectral sensor according to the invention. In FIG. 8, transmittance measurement is shown first, but those skilled in the art will appreciate that transmittance and reflectance may be measured in any order. In this example, transmittance measurement commences 81 and light is emitted from the light source positioned behind the media 82, in this case light source 1. Spectral transmittance is captured 83 and the measurement is validated 84. If validation fails, then a warning message is sent 85; else the spectral value is saved 86.

Reflectance measurement commences by emitting light from the light source positioned above the surface of the media 87, in this case light source 2. Spectral reflectance is captured 88 and the spectral value is saved 89. Validation is performed on the captured value 90 and if validation fails a warning message is sent 91; else the next patch is measured 92.

In an embodiment, an optical block, e.g. optical fiber, lens, etc. is used to send light to the sheet and return light from the sheet. Further, in a presently preferred embodiment, the size of the patch measured should be less than 6×6 mm. The measurement of each patch is performed by a movement of the sheet, of the sensor, or both by a set of stepping motors in a mode that is preferably not X, Y.

Thus, an embodiment captures information for transparency and reflectance for analysis of the ink and substrate opacity. This information is especially useful for grand format printers, such as the Vutek printer.

Apparatus and Process for the Measurement of Reflectance and Halftone Coverage of a Surface It is known to perform a dot coverage estimation, e.g. as performed by the TECHKON SpectroPlate/Plate measurement device or X-RITE iCPlate2. However, dot coverage estimation alone is only of some use, but does not provide sufficient information for modern printing applications. An embodiment of the invention provides an apparatus and process for the measurement of reflectance and halftone coverage of a surface. In an embodiment, an automated measurement is made of spectral reflectance and surface covered by the halftone (see FIG. 9 for all the colored patches present on one sheet (fingerprint).

Figure 9:
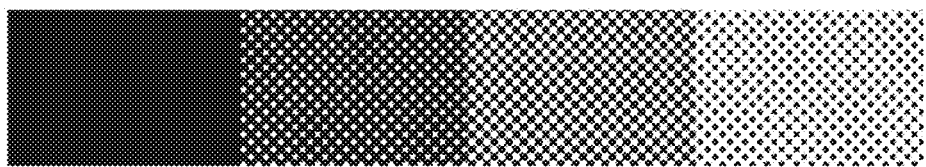
FIG. 9 shows a media surface covered by a halftone image according to the invention.

In FIG. 9, the gradient is printed with one ink and made by halftoning. In this example, the reflectance measurement determines the ratio of light reflected by all of the media surface, i.e. dot and substrate, for each wavelength detected by the sensor. Due to the surface integration, the halftone, e.g. size of the dot, shape, frequency, etc., is not taken in account for the spectral reflectance. A similar value could be obtained for a surface without halftone. In an embodiment, the camera (image sensor) captures an image of the halftone pattern and determines the surface covered by the ink (halftone) on the media, i.e. a ratio of covered surface to uncovered surface, and not a ratio of light reflectance. The light reflected by the surface integrated by the aperture, e.g. 3 mm, is not determined. In embodiments of the invention, a processor applies a numerical filter (color) to perform image analysis and determine a threshold estimate the surface coverage by the ink dot.

Figure 10:
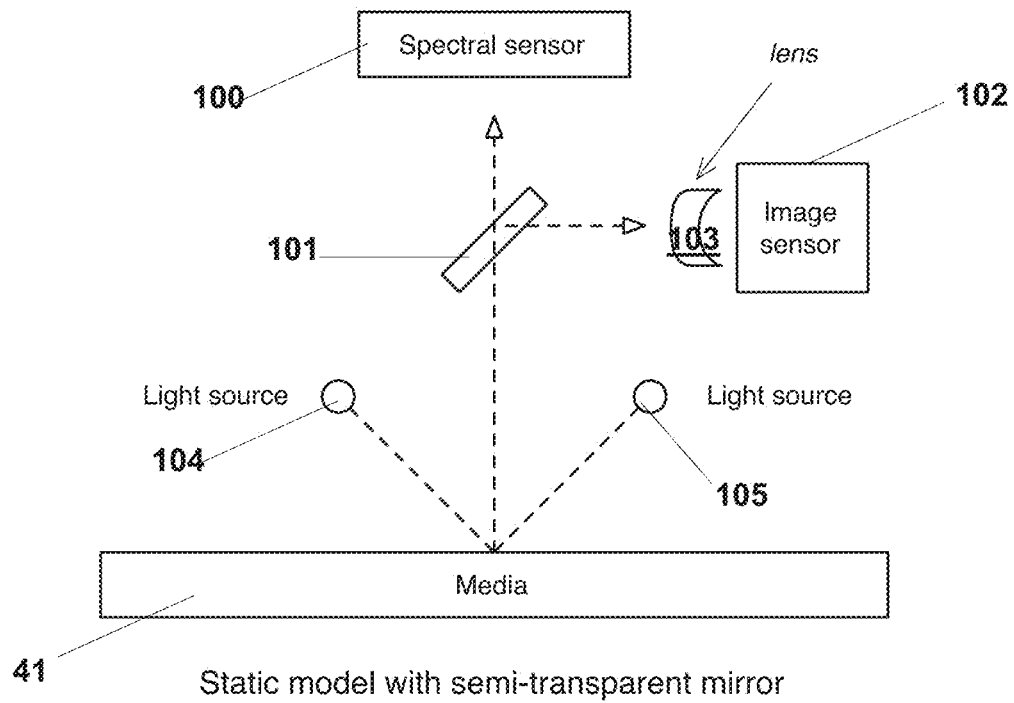
FIG. 10 is a block schematic diagram of a mechanism for measuring spectral reflectance and for image capture according to the invention.

FIG. 10 is a block schematic diagram of a mechanism for measuring spectral reflectance and for image capture according to the invention. In a presently preferred embodiment, one spectral sensor 100 is used to measure the spectral reflectance and one color camera 102, e.g. 1024×1024 pixel, is used for analysis of an imaged surface of the media 41, e.g. 2×2 to 1×1 mm with regard to light emitted onto the media surface by light source 104, 105. In an embodiment of the invention. light deviation is achieved by a semi-transparent mirror 101, such as a beam splitter, that sends the information from the surface of the media through a lens 103 to the image sensor, e.g. CCD or CMOS matrix. A benefit of this embodiment is that there is no movement and a disadvantage is that energy may lost through the semi-transparent mirror.

Figures 11A, 11B:
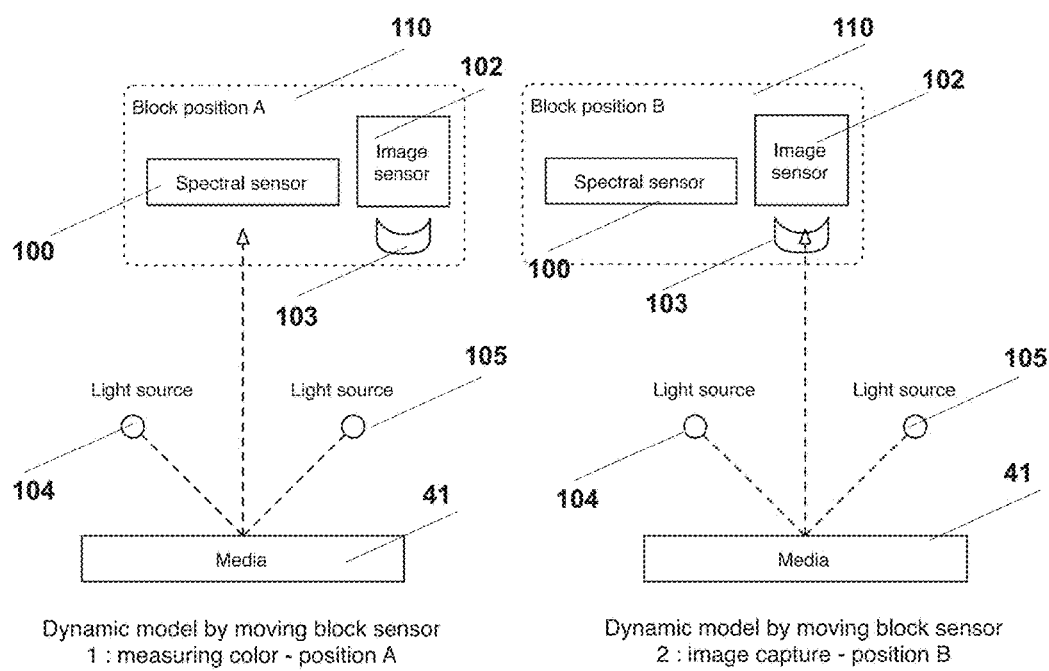
FIGS. 11A and 11B are schematic diagrams showing a mechanism for moving a block sensor from a spectral sensor (FIG. 11A) to an image sensor (FIG. 11B) according to the invention.

FIGS. 11A and 11B are schematic diagrams showing a mechanism for moving a block sensor from a spectral sensor (FIG. 11A) to an image sensor (FIG. 11B) according to the invention. In FIGS. 11A and 11B, a moving sensor block 110, includes a spectral sensor for color measurement 100 and an image sensor 102 and lens 103 for image acquisition. In an embodiment o the invention, the spectral reflectance is first measured (FIG. 11A). The block sensor is then moved to position the image sensor in the same axis as that used for spectral measurement (FIG. 11B). Image acquisition benefits of this embodiment include that there are no light energy losses; risks of this approach may involve the use of moving pieces, e.g. positioning accuracy, wear, etc. In other embodiments of the invention, it is possible to move the sheet, and not move the block sensor. A purpose of the image camera is to get an implied dot area that is better than what one gets from a traditional dot gain measurement of a tint relative to 100% and white.

In both cases, one goal is to capture the spectral reflectance and the dot coverage estimation for the same surface, at the same localization. In embodiments of the invention, two sensors are moved in the X, Y, Z directions, as controlled with high precision by a stepper motor so that, although the measurements for the two sensors are not made simultaneously, they are performed for both sensors in the same position for all patches, e.g. the spectral reflectance is first measured with one sensor for all patches and the image is then captured with the second sensor.

In an embodiment, an optical fiber is used to send light to the sheet and return light from the sheet. Further, in a presently preferred embodiment, the size of the patch measured should less than 6×6 mm. The measurement of each patch is performed by a movement of the sheet, of the sensor, or both by a set of stepping motors in a mode that is preferably not X, Y.

Thus, this embodiment captures information regarding halftone and ink volume variation for spectral reflectance. This information is especially useful for grand format printers, such as the Vutek printer.

Apparatus and Process for Fast Substrate Detection

An embodiment of the invention provides an apparatus and process for fast substrate detection. An embodiment of the invention automatically detects the kind of substrate that is in a printer and proposes any of an automatic loading of a new technical setup, e.g. curves, ICC, etc., and/or provides a warning to the user. On the substrate only, generally before printing, measurement is made of the reflectance, transparency, and gloss with a visible light near to daylight (one source) or two or three colored sources, e.g. blue/red and green. In an embodiment, diode emitting light (DEL) is used for a low cost device.

Figure 12:
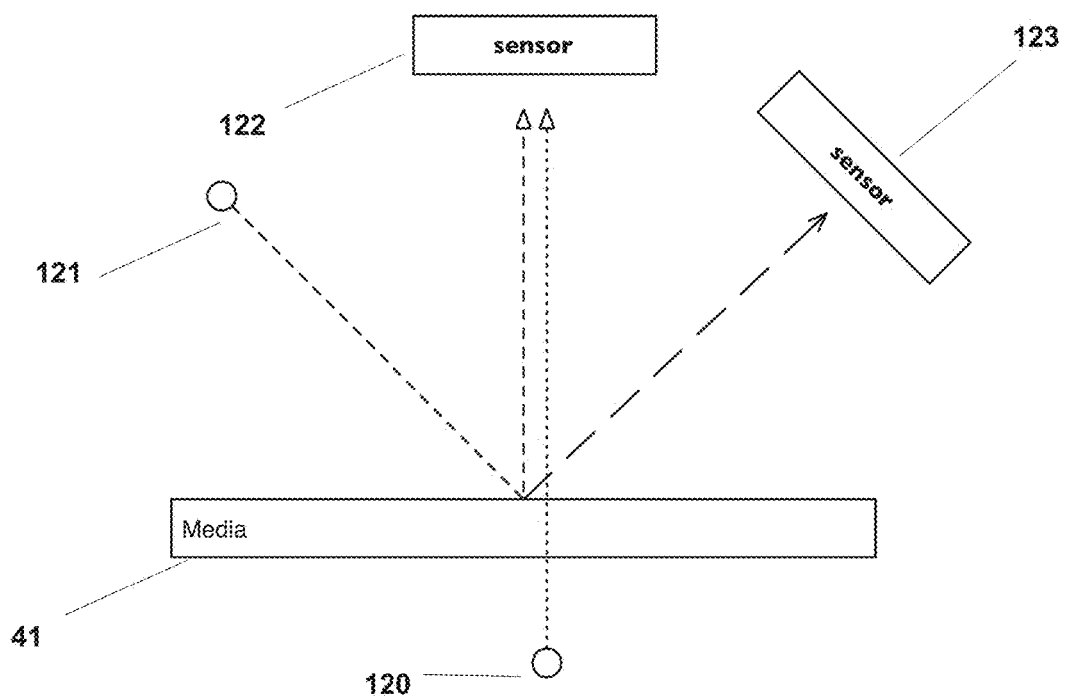
FIG. 12 is a block schematic diagram showing a mechanism for fast substrate detection with regard to color, gloss, and transmittance according to the invention.

FIG. 12 is a block schematic diagram showing a mechanism for fast substrate detection with regard to color, gloss, and transmittance according to the invention. In FIG. 12, a first light source 120 is provided and light is transmitted from the light source, through a medium 41, to a sensor 122.

The sensor for the first light source may be a trichromatic (RGB) or spectral sensor. A second light source 121 is directed to the medium surface and light reflected therefrom is detected by sensors 122 and 123. The sensor 123 is an intensity sensor for specular reflectance at 45°.

Figure 13:
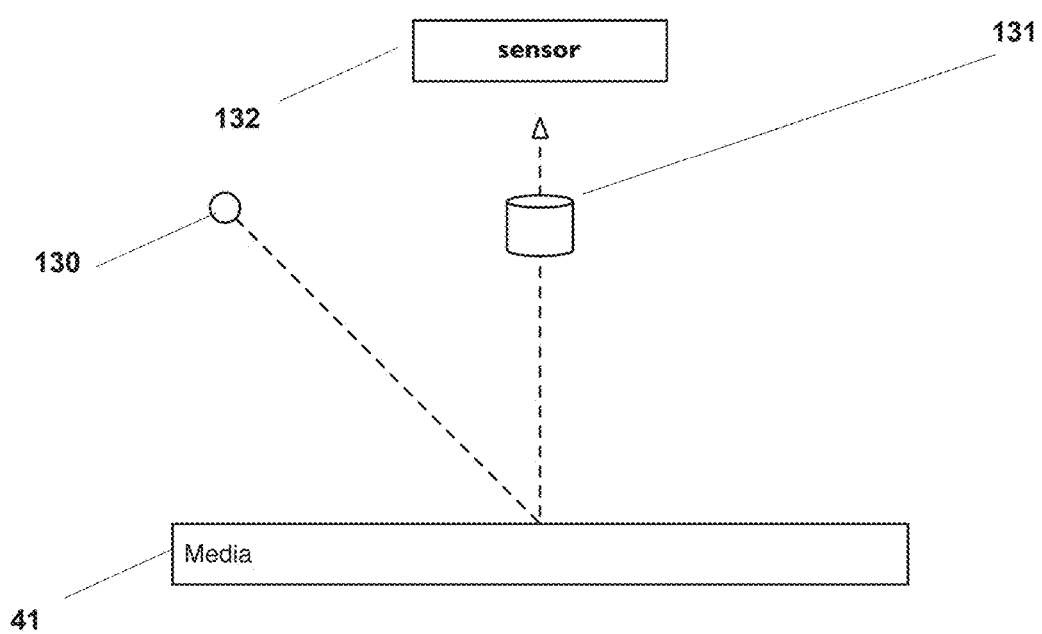
FIG. 13 is a block schematic diagram showing a mechanism for fast substrate detection with regard to texture quantification according to the invention.

FIG. 13 is a block schematic diagram showing a mechanism for fast substrate detection with regard to texture quantification according to the invention. In FIG. 13, a light source 130 is directed to the medium surface. Reflected light is focused through an optical lens 131 onto a sensor 132, which may be a grayscale CCD (or CMOS) device arranged as a bar or matrix.

Figure 14A:
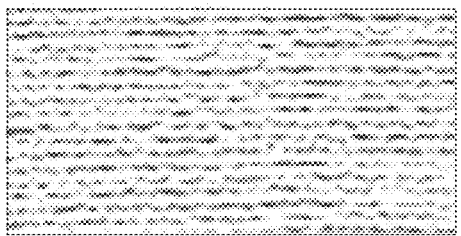
FIGS. 14A-14C are examples of texture quantification and accompanying plots of gray values vs. pixel distance according to the invention.
Figure 14A:
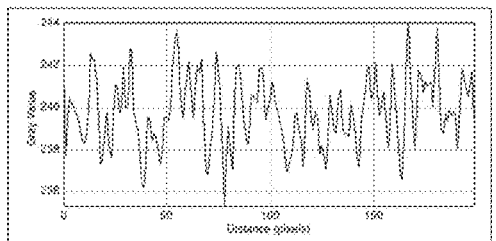
Figure 14B:
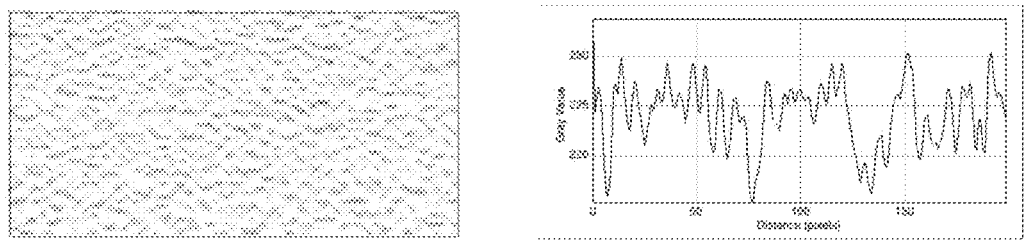
Figure 14C:
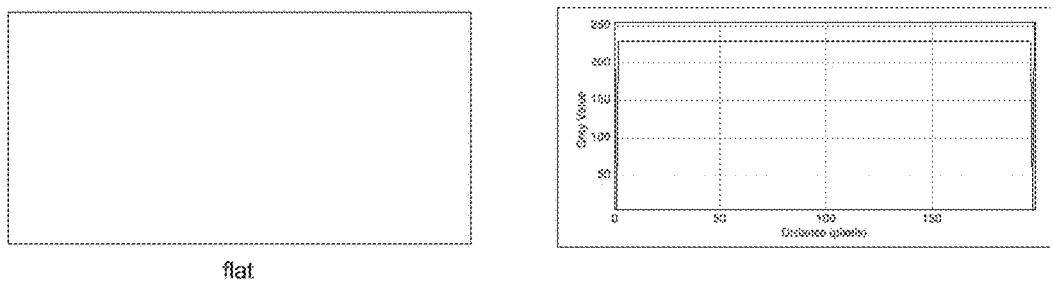

FIGS. 14A-14C are examples of texture quantification and accompanying plots of gray values vs. pixel distance according to the invention.

In an embodiment, an optical fiber is used to send and return light.

The combination of all the information obtained by such measurements results in a unique ID for each substrate. By processing the measurements, it is possible to estimate any of:

Substrate color;
Substrate opacity;
Substrate gloss/mat scale; and
Substrate roughness or texture.

Data Base Fields

Substrate color is measured with a 45/0° geometry in a colorimetric mode, e.g. using a three RGB sensor, or in spectral reflectance mode. Colorimetric data are then computed from spectral reflectance data. The data is saved in $CIEL^*a^*b^*$ (D50/2°), or in another colorimetric space if needed, such as XYZ. This data is referred to herein as REFCLR.

Substrate opacity is measured, in an embodiment of the invention, with one band, e.g. Green band, similar to human intensity perception; or with three bands, e.g. R, G, B band, similar to the colorimeter color filter. The data saved is a measure of relative density, e.g. logarithm of the transmittance, and/or another colorimetric space if needed, such as XYZ. This data is referred to herein as TRINT.

Substrate gloss unit is measured, in an embodiment of the invention, with one sensor and one source light=one degree, e.g. 60° or 45°, with more than one sensor and/or light, e.g. three degrees (20°, 60°, 85°). The data saved is a measure of relative density, e.g. logarithm of the reflectance, and/or relative intensity and/or gloss/unit, standardized after an internal calibration with an official standard. This data is referred to herein as GULVL.

Substrate roughness or texture is measured, in an embodiment of the invention, with one D sensor, such as a CCD bar, and a uniform light source in the visible spectrum or a 2D sensor, such as a CCD photosensor, and a uniform light source in the visible spectrum. After processing the values, the data is saved. This data is referred to herein as TXTLVL.

In an embodiment of the invention, substrate roughness or texture quantification could be accomplished using Laws Texture Energy Measures (see K. Laws, *Textured Image Segmentation*, Ph.D. Dissertation, University of Southern California, January 1980) or by another approach. Laws' approach to generating texture features uses local masks to detect various types of textures. In this approach, convolution masks of 5×5 are used to compute the energy of texture which is then represented by a nine element vector for each pixel. The masks are generated from the following vectors:

L5=[+1 +4 6 +4 +1] (Level)
E5=[-1 -2 0 +2 +1] (Edge)
S5=[-1 0 2 0 -1] (Spot)
W5=[-1 +2 0 -2 +1] (Wave)
R5=[+1 -4 6 -4 +1] (Ripple)

Database Creation

In a laboratory condition, e.g. device calibrated, temperature and hydrometry in accordance to the production standard, these parameters are measured for all the media to be used on the printer. These measurements are saved in a data base (see Table 1, below).

TABLE 1

| | Database Parameters | | | |
|---|---|---|---|---|
| Media ref | Color | Opacity | Gloss | Texture |
| A | REFCLR#1 | TRINT#1 | GULVL#1 | TXTLVL#1 |
| B | REFCLR#2 | TRINT#2 | GULVL#2 | TXTLVL#2 |
| ... | ... | ... | ... | ... |
| X | REFCLR#X | TRINT#X | GULVL#X | TXTLVL#X |

Search Algorithm

A goal of the search algorithm is to find a similar or nearest media type by comparison with the existing values saved in the data base, based upon the values [REFCLR, TRINT, GULVL, TXTLVL] measured for a medium. For example, if a white matte paper without texture is loaded into the printer, where the paper already exists in the data base, then a reference for this media is obtained by processing the measured values, which returns the values from the data base. In another example, if a white matte paper without texture is loaded into the printer, where the paper does not exist in the data base, then the nearest, i.e. similar, reference media is identified in the database by processing the measured values.

For the search algorithm, an embodiment of the invention uses the KD-tree approach. A k-d tree (short for k-dimensional tree) is a space-partitioning data structure for organizing points in a k-dimensional space. k-d trees are a useful data structure for several applications, such as searches involving a multidimensional search key, e.g. range searches and nearest neighbor searches. k-d trees are a special case of binary space partitioning trees.

The nearest neighbor search (NN) algorithm aims to find the point in the tree that is nearest to a given input point. This search can be done efficiently by using the tree properties to quickly eliminate large portions of the search space.

Searching for a nearest neighbor in a k-d tree proceeds as follows:

1. Starting with the root node, the algorithm moves down the tree recursively, in the same way that it would if the search point were being inserted, i.e. it goes left or right depending on whether the point is less than or greater than the current node in the split dimension.
2. Once the algorithm reaches a leaf node, it saves that node point as the current best.
3. The algorithm unwinds the recursion of the tree, performing the following steps at each node:
   If the current node is closer than the current best, then it becomes the current best.
   The algorithm checks whether there could be any points on the other side of the splitting plane that are closer to the search point than the current best. In concept, this is done by intersecting the splitting hyperplane with a hypersphere around the search point that has a radius equal to the current nearest distance. Because the hyperplanes are all axis-aligned this is implemented as a simple comparison to see whether the difference between the splitting coordinate of the search point and current node is less than the distance (overall coordinates) from the search point to the current best.

If the hypersphere crosses the plane, there could be nearer points on the other side of the plane, so the algorithm must move down the other branch of the tree from the current node looking for closer points, following the same recursive process as the entire search.

If the hypersphere does not intersect the splitting plane, then the algorithm continues walking up the tree, and the entire branch on the other side of that node is eliminated.

4. When the algorithm finishes this process for the root node, then the search is complete.

Result

By the kd-tree approach, even if the media measurements do not match well with the preset saved in the database, there is still some knowledge of the media and a printer preset can be loaded in accordance to the media class. For example, if the gloss level is an major value for drop volume, the drop volume can be adjusted in accordance to the gloss level, even if the color of the media does not match well with the nearest media in the data base. In embodiments of the invention, a simple warning can be provided to the user if the wrong media, or a media that is out of tolerance, is loaded. A warning message can also be provided to save time and media consumption because the print result might not otherwise be in accordance to expectations.

Computer Implementation

Figure 15:
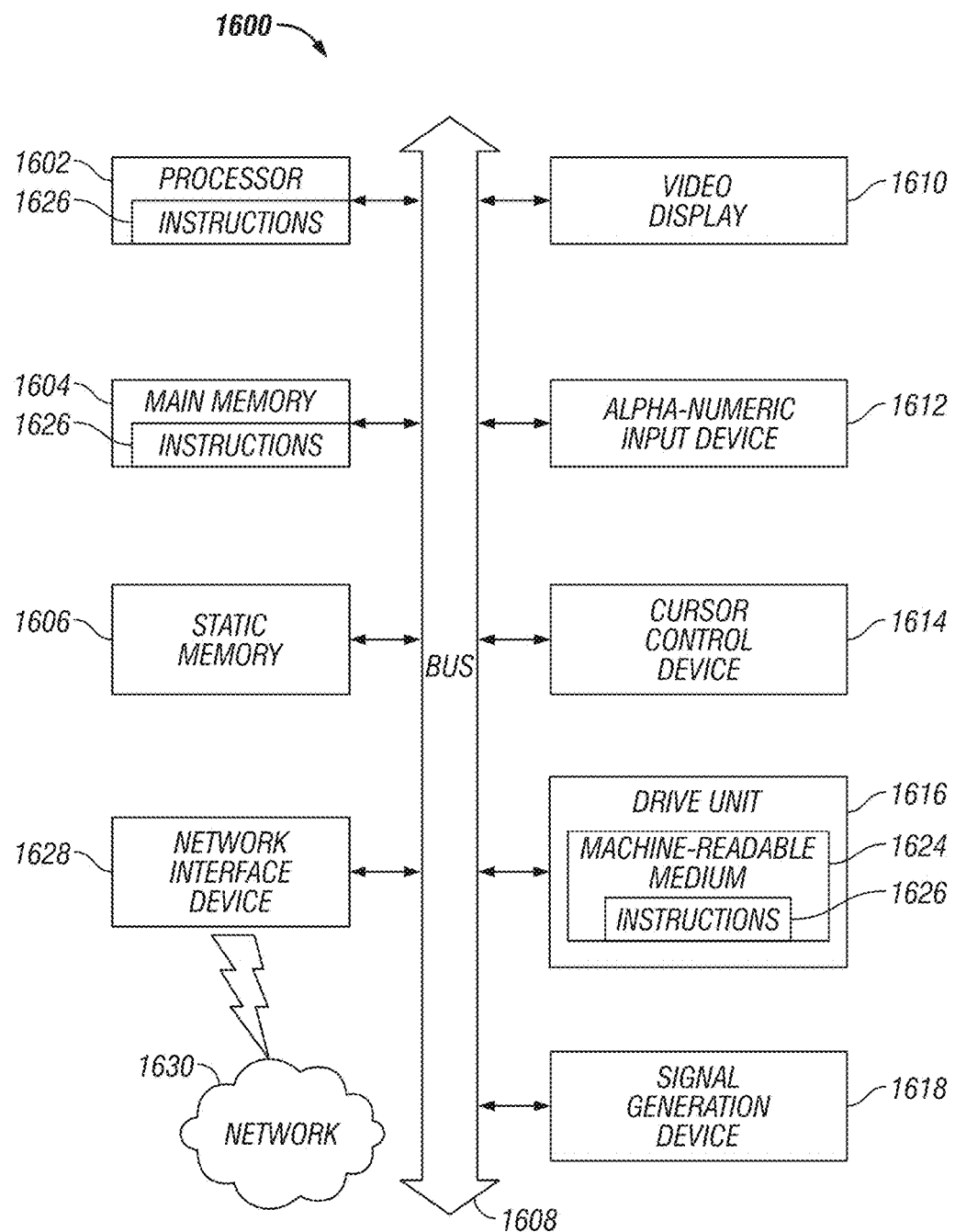
FIG. 15 is a block schematic diagram that depicts a machine in the exemplary form of a computer system within which a set of instructions for causing the machine to perform any of the herein disclosed methodologies may be executed.

FIG. 15 is a block schematic diagram that depicts a machine in the exemplary form of a computer system 1600 within which a set of instructions for causing the machine to perform any of the herein disclosed methodologies may be executed. In alternative embodiments, the machine may comprise or include a network router, a network switch, a network bridge, personal digital assistant (PDA), a cellular telephone, a Web appliance or any machine capable of executing or transmitting a sequence of instructions that specify actions to be taken.

The computer system 1600 includes a processor 1602, a main memory 1604 and a static memory 1606, which communicate with each other via a bus 1608. The computer system 1600 may further include a display unit 1610, for example, a liquid crystal display (LCD) or a cathode ray tube (CRT). The computer system 1600 also includes an alphanumeric input device 1612, for example, a keyboard; a cursor control device 1614, for example, a mouse; a disk drive unit 1616, a signal generation device 1618, for example, a speaker, and a network interface device 1628.

The disk drive unit 1616 includes a machine-readable medium 1624 on which is stored a set of executable instructions, i.e., software, 1626 embodying any one, or all, of the methodologies described herein below. The software 1626 is also shown to reside, completely or at least partially, within the main memory 1604 and/or within the processor 1602. The software 1626 may further be transmitted or received over a network 1630 by means of a network interface device 1628.

In contrast to the system 1600 discussed above, a different embodiment uses logic circuitry instead of computer-executed instructions to implement processing entities. Depending upon the particular requirements of the application in the areas of speed, expense, tooling costs, and the like, this logic may be implemented by constructing an application-specific integrated circuit (ASIC) having thousands of tiny integrated transistors. Such an ASIC may be implemented with CMOS (complementary metal oxide semiconductor), TTL (transistor-transistor logic), VLSI (very large systems integration), or another suitable construction. Other alternatives include a digital signal processing chip (DSP), discrete circuitry (such as resistors, capacitors, diodes, inductors, and transistors), field programmable gate array (FPGA), programmable logic array (PLA), programmable logic device (PLD), and the like.

It is to be understood that embodiments may be used as or to support software programs or software modules executed upon some form of processing core (such as the CPU of a computer) or otherwise implemented or realized upon or within a machine or computer readable medium. A machine-readable medium includes any mechanism for storing or transmitting information in a form readable by a machine, e.g. a computer. For example, a machine readable medium includes read-only memory (ROM); random access memory (RAM); magnetic disk storage media; optical storage media; flash memory devices; electrical, optical, acoustical or other form of propagated signals, for example, carrier waves, infrared signals, digital signals, etc.; or any other type of media suitable for storing or transmitting information.

Although the invention is described herein with reference to the preferred embodiment, one skilled in the art will readily appreciate that other applications may be substituted for those set forth herein without departing from the spirit and scope of the present invention. Accordingly, the invention should only be limited by the Claims included below.

The invention claimed is:

1. A computer implemented method for automatic measurement of reflectance, comprising:
   with at least one spectral sensor of a printer, measuring spectral reflectance at a plurality of angles relative to a sheet for each of a plurality of colored patches on said sheet, the colored patches being formed by the printer to enable real time enhancement of a printing process of the printer;
   processing said measurements by a single angle per measurement independently of each other measurement; and
   successively positioning an optical commutator to successively select an optical receiver from among a plurality of optical receivers, wherein each optical receiver is positioned at a different angle relative to illumination light rays projected from a light source, said optical commutator directing signals from said selected optical receiver to said spectral sensor for measurement of spectral reflectance.

2. The method of claim 1, wherein measurement of each patch is performed by moving any of said sheet, said sensor, or both in other than X, Y coordinates.

3. The method of claim 1, further comprising:
   measuring a next angle of said plurality of angles after a full measurement of said sheet is made for a prior angle of said plurality of angles.

4. The method of claim 1, further comprising:
   measuring spectral reflectance for five angles relative to said sheet.

5. An apparatus for automatic measurement of reflectance, comprising:
   at least one spectral sensor of a printer for measuring spectral reflectance at a plurality of angles relative to a sheet for each of a plurality of colored patches on said sheet, the colored patches being formed by the printer to enable real time enhancement of a printing process of the printer;
   a processor for processing said measurements by a single angle per measurement independently of each other measurement; and an optical commutator for successively positioning the optical commutator to successively select an optical receiver from among a plurality of optical receivers, wherein each optical receiver is positioned at a different angle relative to illuminating light rays projected from a light source, said optical commutator directing signals from said selected optical receiver to said spectral sensor for measurement of spectral reflectance.

6. The apparatus of claim 5, further comprising:
a mechanism for performing measurement of each patch by moving any of said sheet, said sensor, or both in other than X, Y coordinates.

* * * * *